US012778904B2

(12) United States Patent
Fliri

(10) Patent No.: US 12,778,904 B2

(45) Date of Patent: Nov. 3, 2026

(54) HOST DIRECTED DRUG COMBINATIONS FOR TREATMENT OF VIRAL INFECTIONS

(71) Applicant: SystaMedic Inc., Clinton, CT (US)

(72) Inventor: Anton Franz Joseph Fliri, Mystic, CT (US)

(73) Assignee: SystaMedic Inc., Clinton, CT (US)

( * ) Notice: Subject to any disclaimer, the term of this patent is extended or adjusted under 35 U.S.C. 154(b) by 349 days.

(21) Appl. No.: 18/533,681

(22) Filed: Dec. 8, 2023

(65) Prior Publication Data

US 2024/0099991 A1 Mar. 28, 2024

Related U.S. Application Data

(63) Continuation-in-part of application No. PCT/US2022/032650, filed on Jun. 8, 2022.

(60) Provisional application No. 63/208,524, filed on Jun. 9, 2021.

(51) Int. Cl.

| | |
|---|---|
| ***A61K 31/122*** | (2006.01) |
| ***A61K 31/12*** | (2006.01) |
| ***A61K 31/167*** | (2006.01) |
| ***A61K 31/4745*** | (2006.01) |
| ***A61K 31/609*** | (2006.01) |
| ***A61P 29/00*** | (2006.01) |
| ***A61P 31/12*** | (2006.01) |

(52) U.S. Cl.

CPC .......... *A61K 31/122* (2013.01); *A61K 31/167* (2013.01); *A61K 31/4745* (2013.01); *A61P 31/12* (2018.01)

(58) Field of Classification Search

CPC ................ A61K 31/122; A61K 31/167; A61K 31/4745; A61K 31/12; A61K 31/609; A61K 2300/00; A61P 29/00

See application file for complete search history.

(56) References Cited

FOREIGN PATENT DOCUMENTS

| | | | |
|---|---|---|---|
| CN | 106031731 | A | 10/2016 |
| WO | 2003031566 | A2 | 4/2003 |
| WO | 2022120195 | A1 | 6/2022 |

OTHER PUBLICATIONS

CAS printout of JP 200014523 with English abstract (Year: 2000).*

United States Patent and Trademark Office, International Search Report and Written Opinion of the Internatioanl Searching Authority, Application No. PCT/US2022/032650, mailed Oct. 31, 2022, 10 pages.

* cited by examiner

*Primary Examiner* — Brenda L Coleman

(74) *Attorney, Agent, or Firm* — Ziegler IP Law Group, LLC.

(57) ABSTRACT

Drug combinations, compositions including pharmaceutical compositions as well as methods of using and treating a viral infection, including one of the following: (1) atovaquone with a second group of substances consisting of ademetionine, albendazole, celastrol, cepharantine, chloroquine, cycloheximide, diethylstilbestrol, gemcitabine, homoharringtonine, hydroxy progesterone, imatinib, imipramine, indomethacin, ivermectin, niclosamide, raloxifene, sorafenib, and tipifarnib; or (2) cepharantine with a second group of substances consisting of ademetionine, albendazole, atovaquone, celastrol, chloroquine, cycloheximide, diethylstilbestrol, gemcitabine, homoharringtonine, hydroxy progesterone, imatinib, imipramine, indomethacin, ivermectin, raloxifene, sorafenib, and tipifarnib; or (3) one substance selected from a first group of substances consisting of ademetionine, albendazole, atovaquone, celastrol, cepharantine, chloroquine, cycloheximide, diethylstilbestrol, gemcitabine, homoharringtonine, hydroxy progesterone, imatinib, imipramine, indomethacin, ivermectin, raloxifene, sorafenib, tipifarnib in combination with a second group of substances selected from the group consisting of ademetionine, albendazole, celastrol, cepharantine, chloroquine, cycloheximide, diethylstilbestrol, gemcitabine, homoharringtonine, hydroxy progesterone, imatinib, imipramine, indomethacin, ivermectin, raloxifene, sorafenib, and tipifarnib.

8 Claims, No Drawings

HOST DIRECTED DRUG COMBINATIONS FOR TREATMENT OF VIRAL INFECTIONS

FIELD

This disclosure relates to pharmaceutical compositions, pharmaceutical combinations, and methods of treatment of viral infections.

BACKGROUND

Recurrent infections caused by RNA viruses such as influenza and coronaviruses including SAR-CoV-2 threaten economies and millions of lives world-wide. For mitigating detrimental impact on societies caused by these pathogens safe, effective and affordable drugs and drug combinations that can be used for treating viral infections in out of hospital settings are particularly useful. Antiviral drugs have traditionally been developed by directly targeting essential viral components. However, this strategy fails if available drugs become ineffective because viruses rapidly mutate and generate either drug- or vaccine resistant strains. Thus, identifying host cellular factors that are critical for virus replication, but are dispensable for the host, offers a new strategy for antiviral drug development that overcomes the limitation of virus direct approaches because it is less likely that viruses will mutate to replace missing cellular functions which means that targeting host mechanisms for antiviral therapy reduces the chance of generating drug resistant mutants. Moreover discovery of combinations of existing antiviral drugs that, by affecting virus-host-factor interactions, exert synergy allows to increase efficacy of even poorly oral bioavailable antiviral drugs and thereby increases the ability to use such drugs in out of hospital settings.

SUMMARY

In one embodiment, a pharmaceutical composition is provided. The pharmaceutical composition includes atovaquone; and at least one substance selected from a second group of substances consisting of ademetionine, albendazole, celastrol, cepharantine, chloroquine, cycloheximide, diethylstilbestrol, gemcitabine, homoharringtonine, hydroxy progesterone, imatinib, imipramine, indomethacin, ivermectin, raloxifene, sorafenib, or tipifarnib; and a pharmaceutically acceptable carrier.

In another embodiment, a pharmaceutical is provided. The pharmaceutical composition includes cepharantine; and at least one substance selected from a second group of substances consisting of ademetionine, albendazole, atovaquone, celastrol, chloroquine, cycloheximide, diethylstilbestrol, gemcitabine, homoharringtonine, hydroxy progesterone, imatinib, imipramine, indomethacin, ivermectin, niclosamide, raloxifene, sorafenib, or tipifarnib; and a pharmaceutically acceptable carrier.

In another embodiment, a pharmaceutical composition is provided. The pharmaceutical composition includes one substance selected from a first group of substances consisting of ademetionine, albendazole, atovaquone, celastrol, cepharantine, chloroquine, cycloheximide, diethylstilbestrol, gemcitabine, homoharringtonine, hydroxy progesterone, imatinib, imipramine, indomethacin, ivermectin, raloxifene, sorafenib, or tipifarnib; at least one substance selected from a second group of substances selected from the group consisting of ademetionine, albendazole, celastrol, cepharantine, chloroquine, cycloheximide, diethylstilbestrol, gemcitabine, homoharringtonine, hydroxy progesterone, imatinib, imipramine, indomethacin, ivermectin, raloxifene, sorafenib, or tipifarnib; and a pharmaceutically acceptable carrier, wherein the not more than one substance selected from a first group of substances and the at least one substance selected from a second group of substances are not the same.

In another embodiment, a method for treating viral infections in a mammal is provided. The method includes administering to said mammal in need of such treatment an effective amount of one of the above pharmaceutical compositions.

DETAILED DESCRIPTION

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

The use of the terms “a” and “an” and “the” and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., “such as”) provided herein, is intended merely to better illuminate the embodiments and does not pose a limitation on the scope of the claims unless otherwise stated. No language in the specification should be construed as indicating any non-claimed element as essential.

Unless otherwise indicated, all numbers expressing quantities of ingredients, reaction conditions, and so forth used in the specification and claims are to be understood as being modified in all instances by the term “about.” Accordingly, unless indicated to the contrary, the numerical parameters set forth in this specification and attached claims are approximations that may vary depending upon the desired properties sought to be obtained by embodiments of the present disclosure. As used herein, “about” may be understood by persons of ordinary skill in the art and can vary to some extent depending upon the context in which it is used. If there are uses of the term which are not clear to persons of ordinary skill in the art, given the context in which it is used, “about” may mean up to plus or minus 10% of the particular term.

The terms “treating” and “effective amount”, as used herein, unless otherwise indicated, means reversing, alleviating, inhibiting the progress of, or preventing the disorder or condition to which such term applies, or one or more symptoms of such disorder or condition. The term “treatment”, as used herein, unless otherwise indicated, refers to the act of treating as “treating” is defined immediately above. The term “treating” also includes adjuvant and neo-adjuvant treatment of a subject.

Aspects of the present disclosure include novel combinations, pharmaceutical compositions and methods of for treating and/or preventing viral infections in a mammal where the combinations and pharmaceutical compositions comprise atovaquone in combination with at least one substance selected from a second group of substances consisting of ademetionine, albendazole, celastrol, cepharantine, chloroquine, cycloheximide, diethylstilbestrol, gemcitabine, homoharringtonine, hydroxy progesterone, imatinib, imipramine, indomethacin, ivermectin, raloxifene, sorafenib, or tipifarnib or comprise cepharantine with at least one substance selected from a second group of substances consisting of ademetionine, albendazole, atovaquone, celastrol, chloroquine, cycloheximide, diethylstilbestrol, gemcitabine, homoharringtonine, hydroxy progesterone, imatinib, imipramine, indomethacin, ivermectin, niclosamide, raloxifene, sorafenib, or tipifarnib or comprising not more than one substance selected from a first group of substances consisting of ademetionine, albendazole, atovaquone, celastrol, cepharantine, chloroquine, cycloheximide, diethylstilbestrol, gemcitabine, homoharringtonine, hydroxy progesterone, imatinib, imipramine, indomethacin, ivermectin, raloxifene, sorafenib, or tipifarnib in combination with at least one substance selected from a second group of substances selected from the group consisting of ademetionine, albendazole, celastrol, cepharantine, chloroquine, cycloheximide, diethylstilbestrol, gemcitabine, homoharringtonine, hydroxy progesterone, imatinib, imipramine, indomethacin, ivermectin, raloxifene, sorafenib, or tipifarnib, wherein the not more than one substance selected from a first group of substances and the at least one substance selected from a second group of substances are not the same.

In addition, the drug formulations, pharmaceutical compositions, combinations and method of treatment embodiments of the present disclosure can be used not only for humans but also for animals.

Examples of animals include mammals, birds, reptiles, amphibians, and fish.

It has been found that SARS-CoV-2 Is not detectable in the vaginal fluid of women with severe covid-19 infection (See, Qiu L et al. SARS-CoV-2 Is Not Detectable in the Vaginal Fluid of Women with Severe COVID-19 Infection. Clin Infect Dis. 2020 Jul. 28; 71(15):813-817.) For identifying defense mechanisms protecting vaginal tissues in patients with severe SARS CoV-2 infections a topological data analysis approach referred to in U.S. patent Ser. No. 11/120,346, the disclosure of which is incorporated herein by reference in its entirety. For identifying molecular processes which render Vaginal tissues resistant against viral infections in contrast to mucosal tissues of the GI tract and the lung (See, Kumamoto Y, Iwasaki A. Unique features of antiviral immune system of the vaginal mucosa. Curr Opin Immunol. 2012; 24(4):411-416. doi:10.1016/j.coi.2012.05.006). Vaginal tissue proteins were identified that are capable of interacting with SARS CoV-2 interactome proteins referred to in Ostaszewski M., Mazein A., Gillespie M. E. et al. in "(2020) COVID-19 Disease Map. Tissue proteins used in this analysis were derived from the protein atlas (See, Uhlén M., Fagerberg L., Hallström B. M. et al. (2015) Science, 347, 1260419) using a technology referred to in U.S. patent Ser. No. 11/120,346. This comparative analysis identified a set of vaginal tissue proteins directly interacting with the SARS CoV-2 interactome shown in Table 1.

TABLE 1

| Vaginal Tissue network fragments | SARS COV-2 interactome network fragments | Interactions between Vaginal Network and SARS COV-2 Network | Drugs inhibiting SARS COV-2 in VERO 6 cells and affecting Host network nodes |
|---|---|---|---|
| ABL1 | | | sorafenib, homoharringtonine |
| ASNS | | | hydroxy progesterone |
| BAG1 | BAG2 | | atovaquone |
| BAG3 | BAG5 | | chloroquine, celastrol |
| DAPK1 | DDX10 | | sorafenib, Imatinib |
| DDX17 | DDX20 | | ademetionine |
| | DDX21 | | |
| | DDX23 | | |
| | DDX24 | | |
| | DNAJA2 | | |
| DNAJA1 | DNAJA1 | direct overlap | tipifarnib |
| DNAJB6 | DNAJA3 | | |
| HSF1 | DNAJB2 | | indomethacin |
| HSP90AA1 | DNAJC10 | | imatinib |
| | DNAJC19 | | |
| | DNAJC7 | | |
| | HSBP1 | | |
| | HSP90 | | |
| | AB2P | | |
| | HSP90 | | |
| | AB4P | | |
| | HSPA13 | | |
| HSPA1A | HSPA1A | direct overlap | ivermectin |
| HSPA1B | HSPA4 | | albendazole |
| HSPA8 | HSPA4L | | cepharantine |
| HSPB1 | HSPA5 | | imatinib, diethylstilbestrol |
| HSPH1 | HSPA9 | | imatinib |
| ING2 | NME3 | | imatinib |
| NME5 | PSMC1 | | gemcitabine |
| | PSMC2 | | |

TABLE 1-continued

| Vaginal Tissue network fragments | SARS COV-2 interactome network fragments | Interactions between Vaginal Network and SARS COV-2 Network | Drugs inhibiting SARS COV-2 in VERO 6 cells and affecting Host network nodes |
|---|---|---|---|
| PSMC5 | PSMC5 | direct overlap | |
| SF3B4 | SIRT5 | | ademetionine |
| SIRT2 | UBE2G3 | | raloxifene, imipramine |
| UBB | UBE3C | | cycloheximide |
| ZFP36L2 | ZFC3H2 | | |

Network protein identified in Table 1 were then analyzed using the String platform. (See, Szklarczyk D, et al., STRING v11: protein-protein association networks with increased coverage, supporting functional discovery in genome-wide experimental datasets. Nucleic Acids Res. 2019 January; 47:D607-613) which identified that host proteins identified in Table 1 regulate molecular processes associated with cellular stress responses and antigen processing as shown in Table 2.

TABLE 2

| | |
|---|---|
| positive regulation of nucleotide-binding oligomerization domain containing 2 signaling pathway | extrinsic apoptotic signaling pathway via death domain receptors |
| cellular heat acclimation | regulation of transcription from RNA polymerase II promoter in response to hypoxia |
| chaperone-mediated autophagy | positive regulation of mRNA metabolic process |
| positive regulation of microtubule nucleation | negative regulation of protein ubiquitination |
| positive regulation of inclusion body assembly | stem cell division |
| negative regulation of establishment of protein localization to mitochondrion | cellular response to catecholamine stimulus |
| negative regulation of inclusion body assembly | regulation of cellular senescence |
| positive regulation of microtubule binding | negative regulation of extrinsic apoptotic signaling pathway in absence of ligand |
| regulation of inclusion body assembly | response to unfolded protein |
| protein refolding | DNA damage response, detection of DNA damage |
| negative regulation of transcription from RNA polymerase II promoter in response to stress | negative regulation of stress-activated MAPK cascade |
| positive regulation of tumor necrosis factor-mediated signaling pathway | protein folding |
| regulation of cellular response to heat | regulation of intrinsic apoptotic signaling pathway |
| chaperone cofactor-dependent protein refolding | regulation of mRNA stability |
| positive regulation of execution phase of apoptosis | androgen receptor signaling pathway |
| negative regulation of oxidative stress-induced intrinsic apoptotic signaling pathway | negative regulation of fat cell differentiation |
| chaperone-mediated protein complex assembly | positive regulation of interleukin-8 production |
| positive regulation of mRNA splicing, via spliceosome | negative regulation of mitochondrion organization |
| positive regulation of mRNA processing | regulation of mRNA splicing, via spliceosome |
| regulation of mitotic spindle assembly | positive regulation of ATPase activity |
| positive regulation of RNA splicing | negative regulation of apoptotic signaling pathway |
| cellular response to heat | positive regulation of blood vessel endothelial cell migration |
| negative regulation of striated muscle cell apoptotic process | regulation of mRNA processing |
| regulation of transcription from RNA polymerase II promoter in response to stress | regulation of RNA splicing |

TABLE 2-continued

| | |
|---|---|
| regulation of intrinsic apoptotic signaling pathway by p53 class mediator | regulation of mRNA metabolic process |
| positive regulation of erythrocyte differentiation | regulation of protein ubiquitination |
| response to heat | cellular response to hydrogen peroxide |
| regulation of microtubule polymerization | flagellated sperm motility |
| chaperone-mediated protein folding | vascular endothelial growth factor receptor signaling pathway |
| negative regulation of intrinsic apoptotic signaling pathway | |

Next, using again the methodology referred to in U.S. patent Ser. No. 11/120,346, drugs were identified that are capable of interacting with host proteins identified in Table 1 that interact with SARS CoV-2 interactome proteins and, using data published by the National Center for Advancing Translational Sciences (See, Brimacombe, Kyle R et al. An Open Data portal to share COVID-19 drug repurposing data in real time. bioRxiv 2020.06.04.135046), we selected drugs capable of inhibiting SARS Cov-2 replication in Vero 6 cells. These associations are shown on the right in Table 1. For examining effects of drug combinations targeting host proteins involved in the regulation of molecular processes involved in the regulation of stress responses a protein network fragment shown in Table 3 was selected containing proteins that can be targeted by imatinib, atovaquone and cepharantine.

TABLE 3

| HOST Network (H) SARS COV-2 Network (V) DIRECT OVERLAP (DO) | PROTEIN NETWORK NODES | Drugs inhibiting SARS CoV-2 in VERO 6 cells |
|---|---|---|
| H | ASNS | |
| V | NME3 | NICLOSAMIDE |
| H | HSPB1 | |
| H | SIRT2 | |
| V | PSMC1 | |
| H | DNAJB6 | |
| H | DNAJA3 | |
| H | DNAJC10 | |
| H | NME5 | |
| H | SF3B4 | |
| H | ZFP36L2 | |
| V | HSPA9 | |
| H | UBB | |
| H | ING2 | |
| V | PSMC5 | |
| V | DNAJA2 | |
| H | HSPH1 | |
| V | HSPA5 | |
| H | HSP90AA1 | |
| V | DNAJB2 | |
| V | BAG5 | |
| H | BAG3 | |
| V | DDX20 | |
| V | BAG2 | |
| H | ABL1 | |
| H | HSPA1B | |
| DO | HSPA1A | |
| DO | DNAJA1 | |
| H | DDX17 | |
| H | DAPK1 | |
| V | PSMC2 | |
| V | HSBP1 | |
| V | DNAJC7 | |
| H | BAG1 | ATOVAQUONE |
| H | HSF1 | |
| H | HSPA8 | CEPHARANTIN |
| V | SIRT5 | |

For examining effects of drug combinations on the target circuit regulating cellular stress responses shown in Table 2 by targeting either HOST-HOST protein interaction or HOST-VIRUS protein interactions required for viral protein assembly we determined effects of (1) Atovaquone(H) and Niclosamide (V) and (2) Atovaquone (H) and Cephrantin (H) combinations on the viability of SARS CoV-2 infected Vero 6 cells using checkerboard titration virus neutralization assays.

A pharmaceutical composition and embodiments thereof of the present disclosure can be directly using a variety of drug formulations. Such drug formulation contains combinations of active ingredients. Further, the drug formulation can be produced by an arbitrary method that has been well known in the art of drug formulation by mixing the active ingredient with at least one type of pharmacologically acceptable carrier or vehicle. It is desirable that the most effective administration route of drug formulation would be selected for treatment. Examples thereof include oral administration, topical administration and parenteral administration such as intravenous, intraperitoneal, or subcutaneous administration. However, oral administration for treatment of infections in and out of hospital settings is preferable. Examples of dosage forms that can be used for administration include: oral agents such as tablets, powders, granules, pills, suspensions, emulsions, infusions and decoctions, capsules, syrups, liquid, elixirs, extracts, tinctures, and fluid extracts; and parenteral agents such as parenteral injections, intravenous fluids, creams, and Suppositories. The composition in the form of an oral composition is preferably used.

In the case involving the use of liquid preparations such as syrup appropriate for oral administration, the preparations can be formulated by addition of water, Sugars such as Sucrose, Sorbitol, and fructose; glycols such as polyethylene glycol and propylene glycol, oils such as sesame oil, olive oil, and soybean oil; antiseptics such as p-hydroxy benzoate esters; parahydroxy benzoate derivatives such as methyl parahydroxy benzoate; preservatives such as Sodium benzoate; and flavors such as Strawberry flavor and peppermint flavor.

In addition, in the case involving the use of tablets, powders, and granules that are appropriate for oral administration the preparations can be formulated by addition of sugar such as lactose, glucose, sucrose, mannitol, and sorbitol; starch from potatoes, wheat, and corn; an inorganic substance such as calcium carbonate, calcium sulfate, sodium bicarbonate, and sodium chloride; an excipient of a plant-derived powder such as crystalline cellulose, a sweet-root powder and gentian powder, a disintegrator Such as starch, agar, gelatin powder, crystalline cellulose, carmellose sodium, carmellose calcium, calcium carbonate, sodium bicarbonate, and sodium alginate; a lubricant such as magnesium stearate, talc, hydrogenated plant oil, macrogol, and silicone oil; a binder such as polyvinyl alcohol, hydroxypropyl cellulose, methyl cellulose, ethylcellulose, carmellose, gelatin, and starch paste liquid; a surfactant such as fatty acid ester, and a plasticizer such as glycerine.

It is also possible to add an additive generally used for foods and beverages to the drug formulation appropriate for oral administration. Examples of additives include sweeteners, colorants, preservatives, thickening stabilizers, antioxidants, coloring agents, bleaches, antifungal agents, gumbases, bittering agents, enzymes, gloss agents, acidulants, seasonings, emulsifiers, fortifiers, production agents, aroma chemicals, and spice extracts.

The pharmaceutical composition formulation embodiments of the present disclosure appropriate for oral administration may be directly used in the form of, for example, a powder food product, a sheet-type food product, a bottled food product, a canned food product, a retort food product, a capsule food product, a tablet food product, a liquid food product, or a drink. In addition, the drug formulation may be used in the form of food or beverage such as health food, functional food, nutritional supplement, or food for specified health use. For example, a parenteral injection appropriate for parenteral administration comprises preferably a sterilized aqueous agent which contains a composition of the present disclosure and which is isotonic to the blood of a recipient. For example, for a parenteral injection, an injectable solution is prepared with the use of a pharmaceutically acceptable carrier or vehicle comprising a salt solution, a glucose solution, or a mixture of a salt Solution and a glucose solution.

In addition, it is also possible to add at least one supplemental component to a parenteral agent, wherein Such components can be selected from the group consisting of diluents, antiseptics, flavors, excipients, disintegrators, lubricants, binders, surfactants, and plasticizers, which are described above for an oral agent.

An embodiment of the present disclosure includes a combination comprising atovaquone in combination with at least one substance selected from a second group of substances consisting of ademetionine, albendazole, celastrol, cepharantine, chloroquine, cycloheximide, diethylstilbestrol, gemcitabine, homoharringtonine, hydroxy progesterone, imatinib, imipramine, indomethacin, ivermectin, raloxifene, sorafenib, or tipifarnib.

An embodiment of the present disclosure includes a pharmaceutical composition comprising atovaquone in combination with at least one substance selected from a second group of substances consisting of ademetionine, albendazole, celastrol, cepharantine, chloroquine, cycloheximide, diethylstilbestrol, gemcitabine, homoharringtonine, hydroxy progesterone, imatinib, imipramine, indomethacin, ivermectin, raloxifene, sorafenib, or tipifarnib, and a pharmaceutically acceptable carrier.

An embodiment of the present disclosure includes a combination comprising cepharantine with at least one substance selected from a second group of substances consisting of ademetionine, albendazole, atovaquone, celastrol, chloroquine, cycloheximide, diethylstilbestrol, gemcitabine, homoharringtonine, hydroxy progesterone, imatinib, imipramine, indomethacin, ivermectin, niclosamide, raloxifene, sorafenib, or tipifarnib.

An embodiment of the present disclosure includes a pharmaceutical composition comprising cepharantine with at least one substance selected from a second group of substances consisting of ademetionine, albendazole, atovaquone, celastrol, chloroquine, cycloheximide, diethylstilbestrol, gemcitabine, homoharringtonine, hydroxy progesterone, imatinib, imipramine, indomethacin, ivermectin, niclosamide, raloxifene, sorafenib, or tipifarnib, and a pharmaceutically acceptable carrier.

An embodiment of the present disclosure includes a combination comprising one substance selected from a first group of substances consisting of ademetionine, albendazole, atovaquone, celastrol, cepharantine, chloroquine, cycloheximide, diethylstilbestrol, gemcitabine, homoharringtonine, hydroxy progesterone, imatinib, imipramine, indomethacin, ivermectin, raloxifene, sorafenib, or tipifarnib in combination with at least one substance selected from a second group of substances selected from the group consisting of ademetionine, albendazole, celastrol, cepharantine, chloroquine, cycloheximide, diethylstilbestrol, gemcitabine, homoharringtonine, hydroxy progesterone, imatinib, imipramine, indomethacin, ivermectin, raloxifene, sorafenib, or tipifarnib.

An embodiment of the present disclosure includes a pharmaceutical composition comprising one substance selected from a first group of substances consisting of ademetionine, albendazole, atovaquone, celastrol, cepharantine, chloroquine, cycloheximide, diethylstilbestrol, gemcitabine, homoharringtonine, hydroxy progesterone, imatinib, imipramine, indomethacin, ivermectin, raloxifene, sorafenib, or tipifarnib in combination with at least one substance selected from a second group of substances selected from the group consisting of ademetionine, albendazole, celastrol, cepharantine, chloroquine, cycloheximide, diethylstilbestrol, gemcitabine, homoharringtonine, hydroxy progesterone, imatinib, imipramine, indomethacin, ivermectin, raloxifene, sorafenib, or tipifarnib, and a pharmaceutically acceptable carrier.

An embodiment of the present disclosure includes method of using of a pharmaceutical composition or combination embodiment of the present disclosure for the treatment of viral infections in a mammal.

Experimental:

Experiment 1—A virus neutralization assay was performed using Vero E6 cells which are susceptible to SARS-CoV-2 infection. On the day of assay, the monolayer of Vero E6 cells is exposed to a series of dilutions of each test agent, or dilutions of both agents as a combination, in a checkerboard assay format (triplicate wells per dose). Standardized SARS-CoV-2 virus stock calculated to yield approximately $1\times10^2$ $TCID_{50}$/ml is added after 1 hour at 37° C. and 5% $CO_2$, pre-treatment; the plates are incubated for 3 days, and the wells will be scored for the presence or absence of SARS-CoV-2 cytopathic effects (CPE) in the cells. Controls present on each assay plate include Remedesivir as direct acting antiviral compound control (at highest assay concentration) that lacks virus to ensure that the compound itself does not cause CPE. There are also negative control wells (without compound or virus) to verify that the serum-free media does not cause CPE. A back-titer of the virus is performed that serves to verify that the titer of the standardized virus is within an acceptable range. The titer is determined as the inverse of the last dilution of serum that inhibited the viral infection (cells that do not display CPE). Only results are considered when all these controls meet acceptance criteria, Substances meeting these criteria are subjected to checkerboard titration for determining concentration dependency of drug combinations on viral neutralization.

Data from the drug combination are compared to the activity of single agents and to the positive controls used in both in vitro assays and animal studies. The potency of both agents as single drugs and the combination to inhibit SARS-CoV-2 entry and replication in Vero E6 cells (checkerboard titration) is analyzed for each compound's individual minimal inhibitory activity (MIC) and the Fractional Inhibitory Concentration (FIC) index value will be calculated. The FIC index value considers the combination of antivirals that produces the greatest change from the individual antiviral's MIC. To quantify the interactions between the antivirals being tested (calculation of the FIC index is used. The FIC Index value will be used to categorize the interaction of the two antivirals tested, where synergy is defined as a FIC<0.5, additive/indifference as FIC=0.5-4.0, and antagonism as FIC>4.0. The dose-effect curves and $EC_{50}$ values are also compared. This information will provide a range of dose combinations that are synergistic.

Results

| COMBINATION- | | Atovaquone concentration in micromol | | | | |
|---|---|---|---|---|---|---|
| 1 | | 3.30 | 1.10 | 0.37 | 0.12 | 0.00 |
| Niclosamide | 3.30 | CYT | CYT | CYT | CYT | CYT |
| concentration | 1.10 | CYT | CYT | CYT | CYT | 16.67 |
| in | 0.37 | CYT | CYT | 26.19 | 4.76 | 9.52 |
| micromol | 0.12 | CYT | CYT | 26.19 | 11.90 | 11.90 |
| | 0.00 | 50.00 | 16.67 | 9.52 | 2.38 | NA |

Combination experiment 1 shows that Niclosamide is non cytotoxic (CYT) and non-efficacious at concentrations ranging from 0.12 to 1,1 micro mol and that atovaquone is non cytotoxic at concentrations ranging from 0.12 to 3,3 micro molar and inhibits virus induced cytopathic effects (CPE) to 50% at a concentration of 3.3 micro mol. The addition of atovaquone to niclosamide dose dependently increases the cytotoxic effects of niclosamide in that the addition of 1.1 micromole atovaquone renders non cytotoxic concentration of niclosamide (0.12-3.37 micromole) cytotoxic. Atovaquone at a lower concentration of 0.37 micromole marginally increases the efficacy of low doses of niclosamide (0.12 to 0.37 micromolar) which are inactive without the addition of atovaquone. This result suggests that targeting host viral protein interactions can increase antiviral efficacy but within a very narrow margin of safety suggesting that targeting the circuit in table 2 is important for both virus and host.

| COMBINATION- | | Atovaquone concentration in micromol | | | | |
|---|---|---|---|---|---|---|
| 2 | | 3.30 | 1.10 | 0.37 | 0.12 | 0.00 |
| Cepharanthine | 1.10 | 92.86 | 92.86 | 97.62 | 97.62 | 38.10 |
| concentration | 0.37 | 64.29 | 52.38 | 45.24 | 35.71 | 14.29 |
| in | 0.12 | 69.05 | 35.71 | 19.05 | 11.90 | 9.52 |
| micro | 0.04 | 73.81 | 66.67 | 50.00 | 19.05 | 7.14 |
| mol | 0.00 | 50.00 | 16.67 | 9.52 | 2.38 | NA |

Experiment 2—A similar virus neutralization assay to that conducted in Experiment 1 was performed using cepharantine and atovaquone. Experiment 2 shows that neither cepharantine nor atovaquone are cytotoxic at the highest concentration tested. The addition of cepharantine to atovaquone at all doses tested does not affect the cytotoxicity of either drug. Combining atovaquone and cepharantine unexpectedly results in a dose dependent substantially increase in antiviral efficacy to an extent that renders inactive concentration of cepharantine (0.04-0.12 micromole) in combinations with inactive concentration of Atovaquone (0.12-0.37) producing superior antiviral efficacy that approaches the maximal inhibition of atovaquone at the highest doses. Since cepharantine suffers from poor oral bioavailability this result of experiment 2 indicates that the combination of atovaquone with cepharantine has the capacity to lower projected doses needed to achieve antiviral efficacy and, by increasing the antiviral efficacy of poorly orally bioavailable drugs at lower doses, provide antiviral drug combinations with improved therapeutic index and allow to use these combinations in out of hospital setting in a broad range of populations. In addition, the results produced in drug interaction experiment 1 and 2 indicates that targeting Host-Host protein interaction in cellular stress response regulating circuits identified in Table and 2 provides q novel strategy for identifying host directed drug combinations for treatment of viral infections.

In Vivo Efficacy Evaluation

In vivo efficacy evaluation of Atovaquone and Cepharanthine alone and in combination against SARS-CoV-2 in Syrian Golden Hamster Model [Study Protocol Reference:) Syrian hamsters as a small animal model for SARS-CoV-2 infection and countermeasure development. Masaki Imai et al., PNAS 2020, 117(28)16587-16595]

| Route of Administration | Oral | | |
|---|---|---|---|
| group | Atovaquone | Cepharantine | Atovaquone + Cepharantine |
| Dose | 200 mg/kg | 8 mg/kg | 200 mg kg + 8 mg/kg |
| Vehicle | 0.25% Sodium CMC and 0.05% Tween-20, Water | 2% DMSO, 30% PEG300, 5% Tween-80, Wate | 0.25% Sodium CMC and 0.05% Tween-20, Water + 2% DMSO, 30% PEG300, 5% Tween-80, Water |
| Volume per dose | 10 ml/kg | | |
| Dosing regimen | Once daily for 3 days-1 DPI, 2 DPI & 3 DPI | | |

Results

Data Analysis One way ANOVA-Dunnett's multiple comparison test

| Group | Mean Difference (Log10PFU/lung) | Significance? | Summary | Adjusted P Value |
|---|---|---|---|---|
| Infection Control vs. Remdesivir | 0.97 | YES | *** | 0.00 |
| Infection Control vs. Cepharanthine | 0.42 | NO | ns | 0.11 |
| Infection Control vs. Atovaquone | 0.74 | YES | ** | 0.00 |
| Infection Control vs. Cepharanthine + Atovaquone | 1.15 | YES | **** | <0.0001 |

1. Statistically significant reduction in lung viral loads was seen with atovaquone once-a-day treatment at 200 mg/kg in comparison with infection control.
2. Cepharanthine once-a-day treatment at 8 mg/kg exhibited a marginal but statistically not significant reduction in lung viral loads in comparison with infection control
3. Combination treatment of atovaquone and cepharanthine also demonstrated significant reduction in lung viral loads at 4th day post infection.
4. The efficacy outcome for the combination treatment correlated with improved body weights and histopathology of lungs.
5. Overall, the study demonstrated efficacy of atovaquone and cepharanthine combination in hamsters against COVID-19 infection. Results suggest atovaquone and cepharanthine combination as a potential candidate for the treatment of COVID-19.

All publications, including but not limited to, issued patents, patent applications, and journal articles, cited in this application are each herein incorporated by reference in their entirety.

Thus, while there have been shown, described and pointed out, fundamental novel features of the present disclosure as applied to the exemplary embodiments thereof, it will be understood that various omissions and substitutions and changes in the form and details of devices and methods illustrated, and in their operation, may be made by those skilled in the art without departing from the spirit or scope of the present disclosure. Moreover, it is expressly intended that all combinations of those elements and/or method steps, which perform substantially the same function in substantially the same way to achieve the same results, are within the scope of the present disclosure. Moreover, it should be recognized that structures and/or elements and/or method steps shown and/or described in connection with any disclosed form or embodiment of the present disclosure may be incorporated in any other disclosed or described or suggested form or embodiment as a general matter of design choice. It is the intention, therefore, to be limited only as indicated by the scope of the claims appended hereto.

This written description uses examples as part of the disclosure, including the best mode, and also to enable any person skilled in the art to practice the disclosed implementations, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

While there have been shown, described and pointed out, fundamental features of the present disclosure as applied to the exemplary embodiments thereof, it will be understood that various omissions and substitutions and changes in the form and details of compositions, devices and methods illustrated, and in their operation, may be made by those skilled in the art without departing from the spirit or scope of the present disclosure. Moreover, it is expressly intended that all combinations of those elements and/or method steps, which perform substantially the same function in substantially the same way to achieve the same results, are within the scope of the present disclosure. Moreover, it should be recognized that structures and/or elements and/or method steps shown and/or described in connection with any disclosed form or embodiment of the present disclosure may be incorporated in any other disclosed or described or suggested form or embodiment as a general matter of design choice. It is the intention, therefore, to be limited only as indicated by the scope of the claims appended hereto.

The invention claimed is:

1. A pharmaceutical composition comprising: atovaquone; and at least one substance selected from a second group of substances consisting of ademetionine, albendazole, celastrol, cepharantine, chloroquine, cycloheximide, diethylstilbestrol, gemcitabine, homoharringtonine, hydroxy progesterone, imatinib, imipramine, indomethacin, ivermectin, raloxifene, sorafenib, or tipifarnib; and a pharmaceutically acceptable carrier.

2. A pharmaceutical composition comprising: cepharantine; and at least one substance selected from a second group of substances consisting of ivermectin or niclosamide, and a pharmaceutically acceptable carrier.

3. The pharmaceutical composition according to claim 1 wherein the substance selected from the second group of substances is cepharantine.

4. The pharmaceutical composition to claim 1 wherein the substance selected from the second group of substances is ivermectin.

5. A method for treating viral infections in a mammal, the method comprising administering to said mammal in need of such treatment an effective amount of the pharmaceutical composition of claim 1.

6. A method for treating viral infections in a mammal, the method comprising administering to said mammal in need of such treatment an effective amount of the pharmaceutical composition of claim 2.

7. A method for treating viral infections in a mammal, the method comprising administering to said mammal in need of such treatment an effective amount of the pharmaceutical composition of claim 3.

8. A method for treating viral infections in a mammal, the method comprising administering to said mammal in need of such treatment an effective amount of the pharmaceutical composition of claim 4.

* * * * *